(12) United States Patent
Schoedel et al.

(10) Patent No.: US 9,090,543 B2
(45) Date of Patent: Jul. 28, 2015

(54) METHOD FOR PRODUCING DIMETHYL ETHER FROM METHANE

(71) Applicant: LINDE AKTIENGESELLSCHAFT, Munich (DE)

(72) Inventors: Nicole Schoedel, Munich (DE); Ernst Haidegger, Riemerling (DE); Holger Schmigalle, Geretsried (DE); Axel Behrens, Munich (DE); Volker Goeke, Geretsried (DE); Christian Thaller, Munich (DE); Harald Schmaderer, Wolfratshausen (DE)

(73) Assignee: Linde Aktiengesellschaft, Munich (DE)

( * ) Notice: Subject to any disclaimer, the term of this patent is extended or adjusted under 35 U.S.C. 154(b) by 0 days.

(21) Appl. No.: 14/375,891

(22) PCT Filed: Jan. 15, 2013

(86) PCT No.: PCT/EP2013/000102
§ 371 (c)(1),
(2) Date: Jul. 31, 2014

(87) PCT Pub. No.: WO2013/113468
PCT Pub. Date: Aug. 8, 2013

(65) Prior Publication Data
US 2015/0045456 A1    Feb. 12, 2015

(30) Foreign Application Priority Data

Jan. 31, 2012  (DE) .......................... 10 2012 001 803
Jan. 31, 2012  (DE) .......................... 10 2012 001 811
Feb. 21, 2012  (EP) ..................................... 12001135

(51) Int. Cl.
C07C 27/06   (2006.01)
C07C 41/01   (2006.01)
C01B 3/34    (2006.01)
C07C 1/20    (2006.01)
C07C 1/22    (2006.01)

(52) U.S. Cl.
CPC . *C07C 41/01* (2013.01); *C01B 3/34* (2013.01); *C07C 1/20* (2013.01); *C07C 1/22* (2013.01); *C01B 2203/0238* (2013.01); *C01B 2203/062* (2013.01); *C07C 2523/72* (2013.01)

(58) Field of Classification Search
None
See application file for complete search history.

(56) References Cited

U.S. PATENT DOCUMENTS

| | | | |
|---|---|---|---|
| 7,211,606 B2 * | 5/2007 | Baek et al ..................... | 518/700 |
| 7,906,559 B2 | 3/2011 | Olah et al. | |
| 8,440,729 B2 | 5/2013 | Olah et al. | |
| 2006/0235088 A1 * | 10/2006 | Olah et al. ................... | 518/702 |
| 2006/0287405 A1 | 12/2006 | Baek et al. | |
| 2008/0319093 A1 | 12/2008 | Olah et al. | |
| 2011/0054045 A1 | 3/2011 | Olah et al. | |
| 2012/0115965 A1 | 5/2012 | Olah et al. | |

FOREIGN PATENT DOCUMENTS

JP       2000103757 A     4/2000

OTHER PUBLICATIONS

International Search Report for PCT/EP2013/000102 dated Mar. 4, 2013.
English Abstract of JP-2000-103757, Publication Date: Apr. 11, 2000.

* cited by examiner

*Primary Examiner* — Sudhakar Katakam
(74) *Attorney, Agent, or Firm* — Millen, White, Zelano & Branigan, P.C.

(57) ABSTRACT

The invention relates to processes for production of dimethyl ether from methane or natural gas comprising: a dry-reforming step, wherein methane and carbon dioxide are converted into carbon monoxide and hydrogen, and a DME synthesis step, wherein the carbon monoxide and hydrogen formed in the dry-reforming step are converted into dimethyl ether, wherein the dry-reforming step and the synthesis step are carried out at identical pressures or at pressures, which do not differ more than 3 bar, preferably not more than 1 bar.

20 Claims, 1 Drawing Sheet

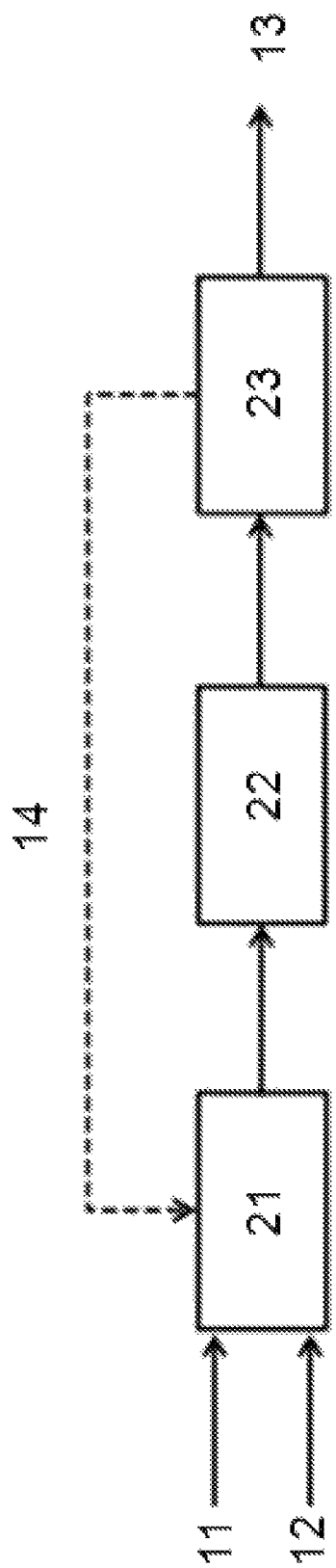

METHOD FOR PRODUCING DIMETHYL ETHER FROM METHANE

The invention relates to a process for production of dimethyl ether from methane.

A process of this type comprises a dry-reforming step, wherein methane and carbon dioxide are converted into carbon monoxide and hydrogen, and a synthesis step, wherein carbon monoxide and hydrogen are converted into dimethyl ether and carbon dioxide.

Dimethyl ether (DME) is obtainable conventionally via the dehydration of methanol (MeOH):

$$2\text{MeOH} \rightarrow \text{DME} + \text{H}_2\text{O}.$$

The methanol is typically obtained from syngas ($H_2$+CO) having a stoichiometric ratio of 2 mol of $H_2$ and 1 mol of CO:

$$2\text{H}_2 + \text{CO} \rightarrow \text{MeOH}.$$

In contrast, there are more recent direct processes which convert syngas having a stoichiometric $H_2/CO$ ratio of about 1:1 into DME in one step:

$$3\text{H}_2 + 3\text{CO} \rightarrow \text{DME} + \text{CO}_2.$$

However, generating syngas from methane or natural gas in a conventional way, for instance by autothermal reforming, steam reforming or partial oxidation, gives $H_2/CO$ ratios significantly greater than 1:1. Therefore, before this gas is used in a direct DME synthesis it has to be adjusted to the correct stoichiometric $H_2/CO$ ratio of about 1:1 and possibly purified.

Production of syngas by dry reforming necessitates costly and inconvenient compression of the syngas before use in the DME synthesis.

Against this background, the problem addressed by the present invention is therefore that of providing a technically simple and economically viable process for synthesizing dimethyl ether from methane.

This problem is solved by a process comprising:
a dry-reforming step, wherein methane and carbon dioxide are converted into carbon monoxide and hydrogen, and
a synthesis step, wherein the carbon monoxide and hydrogen formed in the dry-reforming step are converted into a dimethyl ether and carbon dioxide,
wherein the dry-reforming step and the synthesis step are carried out at identical pressures or at pressures, which do not differ by more than 3 bar, preferably not more than 1 bar.

The process provides that the dry-reforming step and the synthesis step are carried out at essentially identical pressures.

Equalizing the pressure levels of dry reforming and of (direct) DME synthesis makes it possible to save compression stages with their high cost and equipment requirements. It is further in principle possible for the dry reforming to provide a gas mixture which can be used in DME direct synthesis without further purification, modification, compression and/or expansion. Costly and inconvenient apparatus also becomes unnecessary as a result, which is an advantage.

Dry reforming is advantageously carried out in the presence of a modified, soot-resistant nickel-based catalyst as similarly also used in steam reforming. Dry reforming is advantageously carried out at a temperature between 750° C. and 950° C.

Methane for the purposes of the invention also comprehends methane-containing gases such as natural gas.

Dry reforming for the purposes of the invention is to be understood as meaning the conversion of methane or natural gas and $CO_2$ by heating in the absence of water into a syngas having a stoichiometric ratio of about 1:1 for $H_2$ and CO. Dry reforming for the purposes of the invention also comprehends the conversion of $CH_4$ or natural gas and $CO_2$ in the presence of water vapour, although water is only present in a stoichiometric ratio of 1:2, 1:3, 1:4, 1:5, 1:10 or 1:20 in relation to methane or natural gas. In general, dry reforming for the purposes of this invention requires the molar ratio of water to carbon in the feed to be less than 2:1 and preferably less than 1:1.

Synthesis step for the purposes of the invention is to be understood as meaning the direct synthesis of dimethyl ether, in which dimethyl ether is formed directly from hydrogen and carbon monoxide.

Essentially identical pressures for the purposes of the invention are pressures differing from each other by not more than 3 bar, preferably 1 bar, 0.5 bar, 0.3 bar, 0.2 bar and most preferably by not more than 0.1 bar. The pressure between the two synthesis steps differs by the normal pressure drop due to the structural components needed therebetween. Here the pressure, which is given at output of the dry-reforming step, is compared with the pressure, which is given at in input of the DME-synthesis step.

Dry reforming and/or direct dimethyl ether synthesis can be carried out in the presence of suitable catalysts, for instance transition metal catalysts. Advantageous catalysts in dry reforming are particularly modified, soot-resistant, Ni-based catalysts as also used in other steam-reforming processes. The dimethyl ether synthesis is advantageously carried out using copper-based catalysts as also customary in other processes of methanol synthesis.

It is preferable to use for this purpose a Cu-based catalyst which has an acidic functionality for a corresponding high activity and selectivity for DME (bifunctional catalyst). The functionality referred to favours in particular the elimination of water as per $2CH_3OH \rightarrow DME + H_2O$.

In one preferred embodiment of the invention, the process is carried out at a pressure of 20 bar to 50 bar. Elevating the pressure as per this execution of the invention offers various advantages. The reaction equilibrium in the dimethyl ether synthesis becomes shifted to the reaction products. True, the reaction yield of dry reforming becomes slightly diminished, but the elimination of the compression stage offers such technical advantages as to compensate for that.

It is further preferable that no treatment is envisaged for the product gas from dry reforming before entry to DME synthesis, since dry reforming already provides a gas fit for the purpose of direct DME synthesis.

In a further preferred embodiment of the invention, the synthesis step is carried on at least until the dimethyl ether is present in a concentration amounting to not less than 60%, 70%, 80%, 90% or 100% of the equilibrium concentration of dimethyl ether.

The equilibrium concentration of dimethyl ether for the purposes of the invention is to be understood as meaning the dimethyl ether concentration present when the reaction of carbon monoxide and hydrogen to form dimethyl ether and carbon dioxide is in chemical equilibrium. The chemical equilibrium of the reaction is reached when the rate of the forward reaction ($3H_2 + 3CO \rightarrow DME + CO_2$) is equal to the rate of the reverse reaction ($DME + CO_2 \rightarrow 3H_2 + 3CO$).

In a further embodiment of the invention, the product of the synthesis step is separated into a predominantly dimethyl ether-, methanol- and water-containing product phase and a predominantly hydrogen-, carbon monoxide-, carbon dioxide- and methane-containing residual gas.

Such a separation can be brought about for example by cooling and condensing the gas formed in the synthesis step, in which case a condensate consisting predominantly of methanol, water, dimethyl ether and dissolved carbon dioxide and a gaseous phase of hydrogen, carbon monoxide, carbon dioxide and methane are formed. After the condensate has been separated from the gaseous phase, dimethyl ether can be separated from the water and/or methanol by distillation, rectification or sorption.

A product phase consisting predominantly of methanol, water and dimethyl ether for the purposes of the invention is to be understood as meaning in particular that the product phase consists of methanol, water and/or dimethyl ether to an extent of not less than 60%, 70% or 80% (volume percent). Similarly, a residual gas consisting predominantly of hydrogen, carbon monoxide, carbon dioxide and methane is to be understood as meaning in particular that the residual gas consists of hydrogen, carbon monoxide, carbon dioxide and/or methane to an extent of not less than 60%, 70% or 80% (volume percent).

In a further embodiment of the invention, the predominantly hydrogen-, carbon monoxide-, carbon dioxide- and methane-containing residual gas is fed back to the dry-reforming step. This reuse of the residual gas raises the yield of the process and reduces the amount of waste products.

In an alternative embodiment of the invention, the predominantly hydrogen-, carbon monoxide-, carbon dioxide- and methane-containing residual gas is used for providing thermal energy for the endothermic reforming step. Thermal energy can be generated by oxidizing the combustible constituents of the residual gas to form water and carbon dioxide. Supplying thermal energy or heat to the endothermic reforming step can shift the chemical equilibrium of the reforming reaction to the product side (hydrogen and carbon monoxide).

Furthermore dimethyl ether can be preferably converted into a product containing olefins, particularly ethylene and/or propylene, wherein dimethyl ether is fed to the synthesis of olefins directly or only carbon dioxide is separated before fed to the synthesis of olefins.

BRIEF DESCRIPTION OF DRAWINGS

Illustrative embodiments of the invention will now be more particularly described with reference to the figures and related description to elucidate further details and advantages of the invention.

FIG. 1 shows a diagram of the process according to the invention.

EXAMPLE 1

The inventive process (FIG. 1) comprises the combination of dry reforming 21 for syngas production with direct DME synthesis 22 with the two steps being operated at the same pressure level in a pressure range of 20 bar to 50 bar, i.e. without compression or expansion between the dry-reforming step 21 and the DME synthesis step 22.

The product of dry reforming 21 (carbon monoxide and hydrogen) does not have to be subjected to any treatment such as purification, modification of the ratios of carbon monoxide and hydrogen, compression or expansion before entry into the DME synthesis 22, since dry reforming 21 provides a gas fit for the purpose of direct DME-synthesis 22. Equalizing the pressure levels of dry reforming 21 and (direct) DME synthesis 22 saves the compression stage with its high cost and equipment requirements.

Preferably, hydrogen and carbon monoxide are reacted in synthesis step 22 until close to the chemical equilibrium setting for the reaction to form dimethyl ether and carbon dioxide, so the gas formed in synthesis step 22 can subsequently be separated into a predominantly DME/MeOH/$H_2O$-containing product phase 13 and into a predominantly $H_2$/CO/$CO_2$/$CH_4$-containing residual gas 14 (FIG. 1, reference sign 23). The separated residual gas 14 does not have to be purified and reused in the DME synthesis 22, but can be recycled into the dry reforming 21. This results in an improved integration, a significant streamlining of the process and hence lower capital costs.

Alternatively, the residual gas 14 is not recycled as material in dry reforming 21, but can be used energetically to heat the endothermic syngas production 21.

| List of reference signs: | |
| --- | --- |
| 11 | Methane or natural gas |
| 12 | Carbon dioxide |
| 13 | Product phase (DME/methanol/$H_2O$) |
| 14 | Residual gas ($H_2$/CO/$CO_2$/$CH_4$) |
| 21 | Dry reforming |
| 22 | DME direct synthesis |
| 23 | Separation of product gas and residual gas |

The invention claimed is:

1. A process for production of dimethyl ether from methane (11) comprising:
a dry-reforming step (21), wherein methane (11) and carbon dioxide (12) are converted into carbon monoxide and hydrogen, and
a synthesis step (22), wherein the carbon monoxide and hydrogen formed in the dry-reforming step (21) are converted into a dimethyl ether (13) and carbon dioxide,
wherein the dry-reforming step (21) and the synthesis step (22) are carried out at pressures which do not differ by more than 3 bar.

2. A process according to claim 1, wherein the process is carried out at a pressure of 20 bar to 50 bar.

3. A process according to claim 1, wherein a product gas generated by the dry-reforming step (21) and containing said carbon monoxide and said hydrogen is fed directly to the synthesis step (22).

4. A process according to claim 1, wherein the carbon monoxide and hydrogen formed in the dry-reforming step (21) are converted in the synthesis step (22) into dimethyl ether (13) and carbon dioxide until the dimethyl ether is present in a concentration amounting to not less than 60% of the equilibrium concentration of dimethyl ether.

5. A process according to claim 1, wherein the product of synthesis step (22) is separated into a predominantly dimethyl ether-, methanol- and water-containing product phase (13) and a predominantly hydrogen-, carbon monoxide-, carbon dioxide- and methane-containing residual gas (14).

6. A process according to claim 5, wherein the predominantly hydrogen-, carbon monoxide-, carbon dioxide- and methane-containing residual gas (14) is fed to the dry-reforming step (21).

7. A process according to claim 5, wherein the predominantly hydrogen-, carbon monoxide-, carbon dioxide- and methane-containing residual gas (14) is used for providing thermal energy for the dry-reforming step (21).

8. A process according to claim 1, wherein dimethyl ether is converted into a product containing olefins, wherein dimethyl ether is fed to a synthesis of olefins directly or only carbon dioxide is separated from the dimethyl ether before the dimethyl ether is fed to the synthesis of olefins.

9. A process according to claim 1, wherein the dry-reforming step (21) and the synthesis step (22) are carried out at pressures which do not differ by more than 1 bar.

10. A process according to claim 1, wherein the carbon monoxide and hydrogen formed in the dry-reforming step (21) are converted in the synthesis step (22) into dimethyl ether (13) and carbon dioxide until the dimethyl ether is present in a concentration amounting to not less than 70% of the equilibrium concentration of dimethyl ether.

11. A process according to claim 1, wherein the carbon monoxide and hydrogen formed in the dry-reforming step (21) are converted in the synthesis step (22) into dimethyl ether (13) and carbon dioxide until the dimethyl ether is present in a concentration amounting to not less than 80% of the equilibrium concentration of dimethyl ether.

12. A process according to claim 1, wherein the carbon monoxide and hydrogen formed in the dry-reforming step (21) are converted in the synthesis step (22) into dimethyl ether (13) and carbon dioxide until the dimethyl ether is present in a concentration amounting to not less than 90% of the equilibrium concentration of dimethyl ether.

13. A process according to claim 1, wherein dimethyl ether is converted into a product containing ethylene and/or propylene, wherein dimethyl ether is fed to a synthesis of ethylene and/or propylene directly or only carbon dioxide is separated from the dimethyl ether before the dimethyl ether is fed to the synthesis of ethylene and/or propylene.

14. A process according to claim 1, wherein the dry-reforming step (21) is carried out at a temperature of between 750° C. and 950° C.

15. A process according to claim 1, wherein the molar ratio of water to carbon in the feed to the dry-reforming step (21) is less than 2:1.

16. A process according to claim 1, wherein the dry-reforming step (21) and the synthesis step (22) are carried out at pressures which do not differ by more than 0.5 bar.

17. A process according to claim 1, wherein the dry-reforming step (21) and the synthesis step (22) are carried out at pressures which do not differ by more 0.3 bar.

18. A process according to claim 1, wherein the dry-reforming step (21) and the synthesis step (22) are carried out at pressures which do not differ by more than 0.2 bar.

19. A process according to claim 1, wherein the dry-reforming step (21) and the synthesis step (22) are carried out at pressures which do not differ by more than 0.1 bar.

20. A process for production of dimethyl ether from methane (11) comprising:
   a dry-reforming step (21), wherein methane (11) and carbon dioxide (12) are converted into carbon monoxide and hydrogen, and
   a synthesis step (22), wherein the carbon monoxide and hydrogen formed in the dry-reforming step (21) are converted into a dimethyl ether (13) and carbon dioxide,
   wherein no compression or expansion is performed between the dry-reforming step (21) and the synthesis step (22).

* * * * *